United States Patent
Wong et al.

(10) Patent No.: US 10,813,626 B2
(45) Date of Patent: Oct. 27, 2020

(54) SPECTRAL DOPPLER DETECTION

(71) Applicant: Siemens Medical Solutions USA, Inc., Malvern, PA (US)

(72) Inventors: King Yuen Wong, Issaquah, WA (US); Paul D. Freiburger, Seattle, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 888 days.

(21) Appl. No.: 15/198,486

(22) Filed: Jun. 30, 2016

(65) Prior Publication Data

US 2018/0000456 A1    Jan. 4, 2018

(51) Int. Cl.
*A61B 8/08* (2006.01)
*A61B 8/00* (2006.01)
*A61B 8/06* (2006.01)

(52) U.S. Cl.
CPC .............. *A61B 8/488* (2013.01); *A61B 8/06* (2013.01); *A61B 8/08* (2013.01); *A61B 8/469* (2013.01); *A61B 8/5269* (2013.01); *A61B 8/543* (2013.01)

(58) Field of Classification Search
CPC .. A61B 8/06; A61B 8/08; A61B 8/469; A61B 8/5269; A61B 8/543; A61B 8/488
See application file for complete search history.

(56) References Cited

U.S. PATENT DOCUMENTS

| | | | |
|---|---|---|---|
| 4,485,821 A | 12/1984 | Iinuma | |
| 5,664,575 A * | 9/1997 | Banjanin | A61B 8/06 600/455 |
| 6,165,128 A * | 12/2000 | Cespedes | A61B 5/02007 600/463 |
| 6,755,787 B2 | 6/2004 | Hossack et al. | |
| 2007/0167766 A1* | 7/2007 | Takimoto | A61B 8/06 600/437 |
| 2014/0018680 A1* | 1/2014 | Guracar | A61B 8/463 600/440 |

FOREIGN PATENT DOCUMENTS

| | | |
|---|---|---|
| CN | 102046076 A | 5/2011 |
| CN | 103823235 A | 5/2014 |

OTHER PUBLICATIONS

U.S. Appl. No. 14/809,564, filed Jul. 27, 2015.

* cited by examiner

*Primary Examiner* — Bo Joseph Peng

(57) ABSTRACT

In spectral pulsed wave Doppler imaging, spatial variance in signal and/or noise are reduced by combination of multiple spectra with at least partially decorrelated noise. Rather than requiring oversampling in time, the multiple spectra for one Doppler gate are created from different spatial signals. The Doppler gate is divided into sub-gates, the beamformed sample locations in the Doppler gate are grouped into two or more groups using any selection criterion, and/or different receive apertures are used to simultaneously sample the Doppler gate. Spectra for the gate are estimated from the samples with the different spatial content and then combined.

11 Claims, 3 Drawing Sheets

SPECTRAL DOPPLER DETECTION

BACKGROUND

The present embodiments relate to Doppler mode (e.g., spectral) imaging. By transmitting a plurality of pulses (e.g., pulsed wave (PW)) at a location, a Doppler response is generated. For spectral Doppler, the frequency spectrum of the object's motion or flow for a single spatial region is estimated and displayed as a function of time. Spectral Doppler ultrasound imaging provides an image of spectra as velocity values (vertical axis) modulated by energy as a function of time (horizontal axis) for a gate. The spectra may be used for studying fluid flow or tissue motion within a patient.

Spectral Doppler in medical ultrasound is limited in sensitivity due to electronic and acoustic noise and signal processing dynamic range. Other than using better quality electronic components and transducers, the noise may be reduced using image processing. For example, speckle noise is located in a Doppler strip and reduced. As another example, edges between noise and actual signal are found in the Doppler strip and enhanced. These processes use post-processing non-linear filters, but may not sufficiently reduce speckle or other variance.

Another approach is to oversample the signals relative to the user established velocity scale and to create different data sets for the gate at a given time from the oversampling. Spectra are estimated from the different data sets and the resulting spectra combined into a spectrum with less speckle. This approach fails when oversampling is not achievable, such as in the case of fast flow requiring a high sampling rate or when the sample volume is so deep that oversampling is prohibited by round-trip time.

BRIEF SUMMARY

By way of introduction, the preferred embodiments described below include methods, systems, computer readable media, and instructions for spectral Doppler imaging. To reduce spatial variance in signal and/or noise, multiple spectra with at least partially decorrelated noise are combined. Rather than requiring oversampling in time, the multiple spectra for one Doppler gate are created from different spatial signals. The Doppler gate is divided into sub-gates, the beamformed sample locations in the Doppler gate are grouped into two or more groups using any selection criterion, and/or different receive apertures are used to simultaneously sample the Doppler gate. Spectra for the gate are estimated from the samples with the different spatial content and then combined.

In a first aspect, a method is provided for spectral Doppler imaging. An ultrasound system acquires first and second sets of samples representing response from a range gate with first and second spatial content, respectively. The first spatial content is different than the second spatial content. A Doppler estimator estimates first and second spectra for the range gate from the samples of the first and second sets, respectively. Information for the two or more spectra are combined into a combined spectrum. A spectral Doppler strip is displayed as a function of the combined spectrum.

In a second aspect, a method is provided for pulsed wave Doppler imaging. An ultrasound system acquires samples representing a plurality of locations in a user-defined Doppler gate in a patient. A Doppler estimator estimates a plurality of spectra where each of the spectra are estimated from samples for different groupings of the locations. The spectra are combined into a combined spectrum. A spectral Doppler strip as a function of the combined spectrum is displayed.

In a third aspect, a system is provided for pulsed wave Doppler imaging. A beamformer is configured to sample a gate at a pulse repetition interval established in response to a velocity scale. A Doppler estimator is configured to generate multiple pulsed wave spectra from the sampling of the gate. Each of the pulse wave spectra is responsive to different spatial aspects of the gate. A processor is configured to combine the pulsed wave spectra. A display is configured to display a spectrum from the combination.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Interpretation of pulsed wave spectral imaging is often hindered by the "speckly" looking spectrum and background noise, blurring the boundaries between signal and noise. Ultrasound spectral pulsed wave Doppler detectability may be improved. By creating samples responsive to different spatial content, multiple spectra may be estimated for a given Doppler gate with or without also oversampling in time. Spectral variances are reduced by combining multiple spectra with, at least partially, uncorrelated noise. By reducing the variance of signal and noise, a user may more easily distinguish flow from noise.

Multiple spectra are generated in a way that does not require oversampling in time, so the improvement in detectability is not limited by temporal sampling constraints. The multiple spectra are generated by: subdividing the sample volume into sub-gates, which overlap or not; using multiple receives per transmit with overlapped receive apertures; spatially sub-sampling the gate to create multiple subsequences; or combinations thereof. For example, multiple receive lines in a same gate with overlapped receive apertures per transmit are acquired from a single PW sample volume. Multiple pulsed wave spectra are also generated per receive line at the same single sample volume by subdividing the sample volume into overlapping sub-gates. By adjusting the degree of overlapping of receive apertures and/or sub-gates, uncorrelated noise to varying degrees may be achieved in each of the spectra. A compound spectrum is formed by a weighted average of these individual spectra. Statistically, this compound spectrum exhibits reduced spectral variance in both signal and noise, and thus improves flow detectability.

Figure 1:
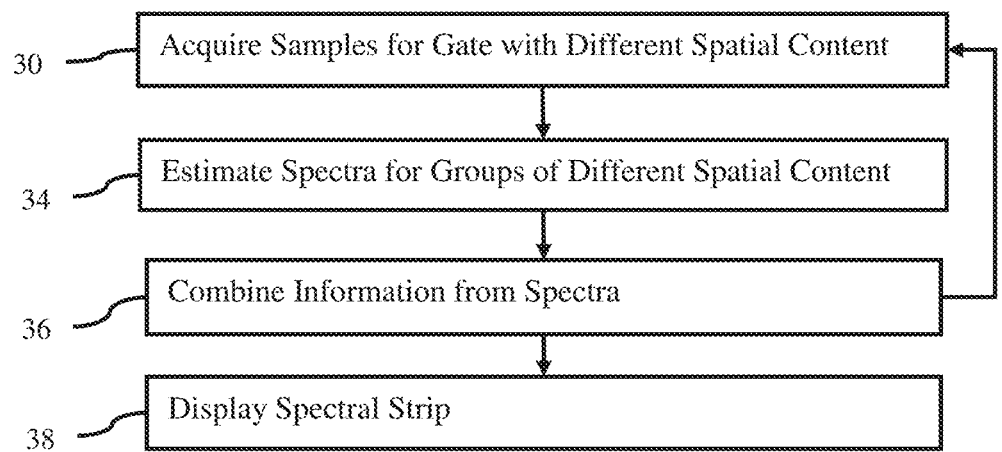
FIG. 1 is a flow chart diagram of one embodiment of a method for spectral pulsed wave Doppler imaging.

FIG. 1 shows a method for pulsed wave spectral Doppler imaging. By acquiring samples with different spatial content for a given Doppler gate, different spectra are estimated for the same Doppler gate representing the flow or motion at a same time. The samples are divided into two or more groups with at least partially independent noise. By combining information from the spectra estimated from the different groups, the speckle or variance may be reduced.

The method is implemented for pulsed wave (PW) spectral Doppler. In PW, a gate location is sampled using pulsed wave (e.g., each pulse using a waveform of 1-50 cycles) transmissions interleaved with echo reception. PW may interleave with other modes of imaging, such as B-mode or flow-mode.

For spectral Doppler imaging, the sample gate, range gate, or spectral Doppler gate is positioned. For example, a B-mode and/or flow-mode scan is performed. The user indicates a gate location on the resulting image. In other examples, the gate is automatically positioned, such as at a location of greatest Doppler velocity or energy determined from flow-mode data. The user or automated process also determines the size of the gate, such as a depth or length in range. The lateral extent and/or range extent may be a default, based on data, user set, or otherwise selected.

Figure 7:
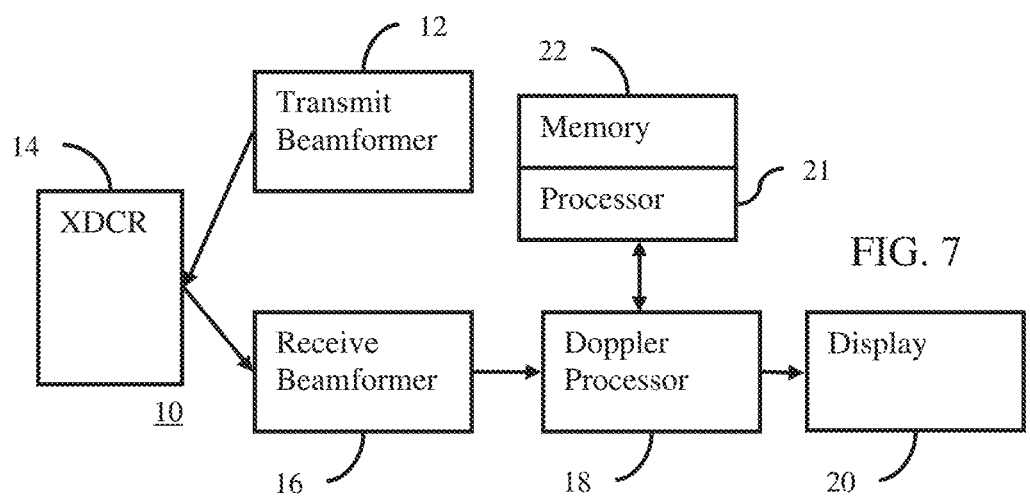
FIG. 7 is a block diagram of one embodiment of a system for spectral Doppler imaging.

The method is implemented by the system 10 of FIG. 7 or a different system. The ultrasound system, such as a beamformer and transducer, acquire samples. A processor, such as a Doppler estimator, separates the samples, estimates spectra, and combines information from the spectra. The ultrasound system displays an image with reduced variance based on the combination. A processor controls the acts. One or more acts may be performed through interaction with a user. Other acts or all the acts may be performed automatically without user input other than initial activation or gate location determination.

The acts are performed in the order shown, but other orders are possible. Additional, different, or fewer acts may be provided. For example, act 38 may not be performed. In yet another example, acts for gate placement, gate sizing, velocity scale setting, pulse repetition frequency setting, filtering, processing, maximum velocity determination over time, or other Doppler functions are provided.

In act 30, the ultrasound system acquires samples representing a range gate location. The samples are beamformed samples, but may be other raw data (e.g., channel data). In alternative embodiments, the samples are acquired by loading from memory or transfer from another device.

For acquisition by scanning, a transducer transmits a plurality of beams of acoustic energy in a sequence. The acoustic or ultrasound energy of each transmission is focused at or near the gate. A sequence of transmissions is performed. The repetition allows reception of sufficient samples to perform spectral or other Doppler analysis. Any ensemble number, such as 3-512, of transmit beams are transmitted so that a spectrum of the response from the Doppler gate may be estimated.

By performing additional transmissions, additional information is obtained for estimating spectra at other times. A given response to a given beam may be used for different spectra (i.e., different times), such as where a moving window of received responses is used to generate each spectrum.

A sufficient number of samples are acquired for a velocity scale set for the spectral Doppler imaging. The ultrasound system uses the velocity scale for the imaging. The velocity scale defines a range of frequencies over which the spectra or velocity is estimated and displayed. The velocity scale is selected or set to avoid aliasing in the estimation of the velocity of flow or motion. The velocity scale is selected by the user, a default or predetermined value of the system, and/or is adaptively determined by the ultrasound system. Based on the velocity scale, the transmissions are performed at a pulse repetition frequency sampling the motion or flow signal at the gate location.

In response to the transmissions, the transducer receives acoustic echoes. A receive beamformer samples the echoes to acquire received signals for the gate. Receive beams are formed by focusing the received signals to coherently combine data representing the gate. This combined data representing the gate are beamformed signals or samples.

The receive operation occurs repetitively in response to the repetitive transmissions. Beamformed samples from the gate location at different times are received. Samples for the same location are acquired over time in an ensemble. For Doppler analysis, an ensemble of samples from a same location is acquired. The samples may be obtained in an ongoing manner such that a moving window (e.g., ensemble or flow sample count) with any step size (e.g., every sample or every third sample) is used to estimate a spectrum.

Figures 2, 3, 4:
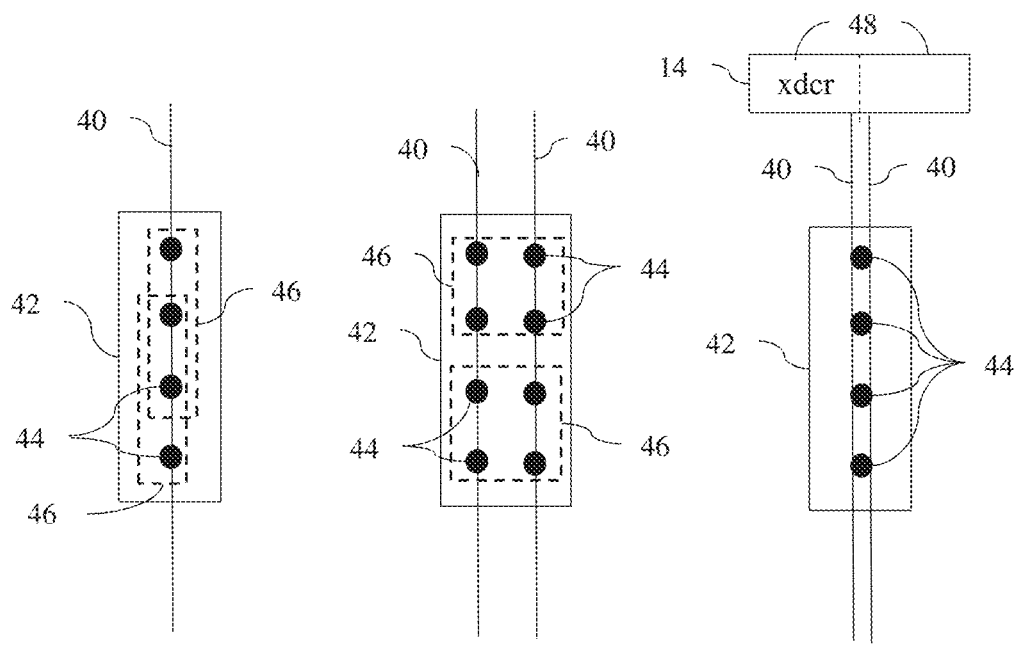
FIG. 2 illustrates example sources of different spatial content for a Doppler gate using sub-gates.
FIG. 3 illustrates example sources of different spatial content for a Doppler gate using sub-gates with parallel receive.
FIG. 4 illustrates example sources of different spatial content for a Doppler gate using different receive apertures.

The receive beamformer samples at any number of locations within the Doppler gate. For example, the lateral extent and/or range extent of the Doppler gate cover two or more beamforming sampling locations. FIG. 2 shows four sample locations 44 along a receive scan line 40 within the Doppler gate 42. FIG. 3 shows eight sampling locations 44. The samples are acquired for a plurality of locations in the user or system-defined Doppler gate in a patient.

The ultrasound system acquires samples representing response from within the gate for each of the locations. The transmissions at the pulse repetition frequency are used to acquire samples from the various locations. In response to each transmission, samples from different locations are acquired. The samples represent the same time or period, but at different spatial locations. In alternative embodiments, samples are acquired for only one beamformer sample location in the gate, but using parallel receive with different receive apertures for variance in spatial content.

The use of different apertures and/or sampling at multiple spatial locations within the gate provide samples with different spatial content. The responses from the range gate have different spatial content.

The samples are separated into two or more groups or sets. The separation is by label, such as setting a flag for each beamformer sample location. Alternatively, the samples of each group are copied to specific memory locations for the groups. In other alternatives, the separation is implemented by loading from designated memory locations as needed. Other separations may be used.

By having each group or set of samples be spatially unique, the groups represent an at least partially independent noise sampling. Some samples may be included in more than one group, but having at least one beamformer sample location in one group and not another provides for difference in spatial content. The noise is, at least partially, sampled independently for each group. To provide this independence, the samples for the entire gate are not filtered across the samples prior to separation. A temporal, anti-aliasing, or clutter filter is not applied to the samples before separation into groups. Any filtering, such as for band limiting in signal-to-noise enhancement, is applied to the samples of each group separately.

FIGS. 2-4 represent different approaches for grouping the samples for a given time or period to provide different spatial content between the groupings. M groups of samples for estimating a respective M spectra are defined. Each group has samples with different spatial content.

FIG. 2 shows use of sub-gates. In this example, there are four beamformer sample locations 44 within the Doppler gate 42. A receive beam is formed along the scan line 40 in response to each transmission, so samples are acquired at the four sample locations 44 in response to each transmission.

The acquired samples are placed into different sub-gates 46. Each sub-gate 46 includes only some of the locations 44 within the user or system established gate 42. One sub-gate 46 may include all of the locations, but the different sub-gates 46 include different combinations of the locations 44. In the example of FIG. 2, one sub-gate 46 includes the top three locations 44 and the other sub-gate 46 includes the bottom three locations 44, resulting in the center two locations 44 being in both sub-gates and the top and bottom locations 44 in only one of the sub-gates 46. Additional sub-gates 46 may be provided. The number of locations 44 in the sub-gates 46 is equal or unequal (FIG. 2 shows equal). More or less overlap of the sub-gates 46 (i.e., shared sample locations 44) may be used. No overlap may be used, such as shown in FIG. 3.

FIG. 2 shows acquiring with the sub-gates 46 overlapping but covering different ranges of depths within the range gate 42. In other embodiments, the sub-gates 46 have different lateral extent, such as sub-gates 46 having a same depth extent but for different laterally spaced scan lines 40 within the range gate 42.

FIG. 3 shows an example where parallel receive beamformation is used. The samples for the sub-gates 46 represent the range gate 42 at the same time or period. In response to each transmit beam, one or more receive beams are formed. FIG. 2 shows forming one receive beam per transmit for spectral Doppler imaging. FIG. 3 shows forming two receive beams per transmit. Three or more receive beams may be formed in response to a given transmission. Where two or more receive beams are simultaneously formed, the samples may be collected along two or more scan lines 40. Since samples locations 44 are distributed in two or three-dimensions rather than just along range, the division into sub-gates 46 includes lateral with or without range separation of the locations 44 into groups of samples with different spatial content.

FIG. 3 shows the sub-gates 46 each including four locations 44 (assuming two-dimensional distribution of locations 44). The sub-gates 46 do not overlap. In other embodiments, the sub-gates 46 overlap in range, such as shown in FIG. 2. In yet other embodiments, the sub-gates 46 establish different spatial content by having a same range extent or coverage but different lateral extent or coverage (e.g., one sub-gate 46 for the locations 44 along one line 40 and another sub-gate 46 for the locations along another line 40). Any combination of locations may be used.

In one embodiment, the locations 44 included in each grouping are based on spatial extent of contiguous sub-gates 46 (i.e., the locations 44 in a given sub-gate 46 are adjacent along orthogonal lines or x, y, z dimensions to each other). In other embodiments, non-contiguous sub-gates 46 are used. For example, the locations 44 are labeled by number in rows by column. Other labeling may be used. Every other location 44 (e.g., even) are included in one sub-gate 46 and the other locations 44 (e.g., odd) are included in another sub-gate 46. Any sampling or selection of the locations 44 may be used for a given grouping.

FIG. 4 shows another approach to grouping samples with different spatial content using parallel receive beamformation. The locations 44 are along a same line with the same locations 44 being used in each grouping. Only one location 44 is needed for the range gate 42, but four are shown in this example. To provide the difference in spatial content for the samples of each grouping, the samples are acquired with different receive apertures 48 of the transducer 14. Different groupings of elements of the transducer 14 array are used to form different receive beams. The receive apertures 48 include contiguous groups of elements, but dis-contiguous groupings of elements may be used. The receive apertures 48 of FIG. 4 do not share any elements (e.g., left half/right half), but overlapping (i.e., sharing elements) receive apertures 48 may be used (e.g., right ⅔ of elements and left ⅔ of elements).

Due to the different groupings of elements, the receive scan lines 40 may be offset from each other. Alternatively, two or more distinct apertures are used to provide the identical scan line 40 for the different receive apertures 48. Each receive aperture 48 is used to separately beamform samples at the locations 44 in response to each transmit beam. The spatial content of each group of samples from corresponding locations 44 is different due to the difference in the receive aperture 48.

These responses (e.g., beamformed samples or channel data used for beamforming) are stored in a memory, such as a main memory, corner turning memory, or CINE. The responses to the Doppler transmissions are stored. This raw Doppler data prior to estimation is stored in an ongoing manner, such as storing the beamformed samples as acquired at a rate at the set or higher PRF.

The storage may be a first-in, first-out or other storage format. For example, the beamformed samples used to generate one or more spectra using multiple passes or estimations are stored. To use the same samples to estimate multiple spectra with the same Doppler estimator, the samples are stored to provide the processing in sequence. Alternatively, parallel processing is used so the samples are stored for less time. Where a moving window is used to estimate for different times, a given sample may be used in the estimations for different times. The samples are stored to account for this overlap. Alternatively, a greater or lesser number of responses are stored.

The samples may be duplicated where the samples for the same location 44 are used in more than one group (e.g., sub-gate 46). The samples for a same location 44 may be stored in more than one location, such as where samples for a given group are windowed and accumulated separately from samples for another group. Alternatively, the desired samples are loaded from memory as needed when estimating for a given group.

The samples of each group or set may be filtered. For example, the accumulated samples for each group are clutter filtered to remove frequency content or velocity associated with undesired motion (e.g., remove slow tissue related movement where the spectral estimation is for flow or vise versa).

In act 34 of FIG. 1, a Doppler estimator estimates two or more spectra for the Doppler gate from the samples of the two or more groups, respectively. M spectra are estimated from the M groups. Each spectrum has at least a partially independent representation of noise and/or signal.

Each spectrum represents the energy as a function of frequency or velocity for a same time or period. Frequency has a known relationship to velocity, so expression in terms of frequency provides velocity and expression in terms of velocity provides frequency. Each spectrum represents the energy as a function frequency over the range and/or lateral extent of the range gate. Due to the selection of locations, different spatial extents of the range gate are represented. Alternatively or additionally, the same spatial extent is represented but with different spatial content from use of different receive apertures.

The Doppler estimator estimates the spectra from the responses or samples of a group. Spectra are estimated for the Doppler gate. The spectra are estimated by applying a Fourier transform, wavelet transform, or Wigner-Ville distribution to the sequence of ultrasound responses or samples. Any transform may be applied to determine the spectra.

The spectra are estimated using the velocity scale. The signal from the fluid or tissue is over a range of positive and negative velocities. The range used in the estimation is the velocity scale. Any velocities beyond the velocity scale wrap around or are aliased. The spectra provide energy as a function of frequency over the range of frequencies set by the velocity scale.

The spectra are estimated from the ultrasound samples in the sequence of samples from the Doppler gate. Each spectrum corresponds to a period in which the samples were acquired. The spectra estimated from the different groups represent a same time or the period.

The spectra result from samples with different spatial content. For example, each of the spectra are estimated from samples with different groupings of locations within the range gate. Different depth and/or lateral groupings of the locations are used. Different sub-sampling of the locations may be used (e.g., 3N and 3N+1 in one group and 3N+1 and 3N+2 in another group). The groupings of locations have any amount of overlap, but one grouping includes samples from at least one location not in another grouping. Other groupings may be for different receive apertures. The spectra estimated from the samples from the different groupings have, at least partially, decorrelated variance in the noise and/or signal.

In act 36, the Doppler estimator or other processor combines information for the two or more spectra into a combined spectrum. In one embodiment, the spectra representing the same gate at a same time are summed. For each velocity or frequency, the corresponding energies are added. Alternatively, the spectra are averaged, which includes summing. The resulting spectrum may be filtered. Other combination functions of the spectra may be used, such as combination by peak detection. Weighted combination may be used. Some spectra may be more heavily weighted than others or equal weighting is used.

In another embodiment, the separately estimated spectra are further processed separately, such as taking a square root, applying log or other compression, and mapping to display values. The combination occurs at any point along the process. For example, the pixel or display values from the different spectra for a given time are averaged. Each spectrum is mapped to a column of pixels to represent the spectrum of response for the gate location. Each pixel in the column is for a same time, but different velocity. The pixel value is mapped from the energy of the spectrum. Since this mapping occurs for each spectrum representing that time, an average of the display values for each pixel is calculated, providing a combined spectrum as display mapped. Other combinations at other points in the process may be used.

Figure 5:
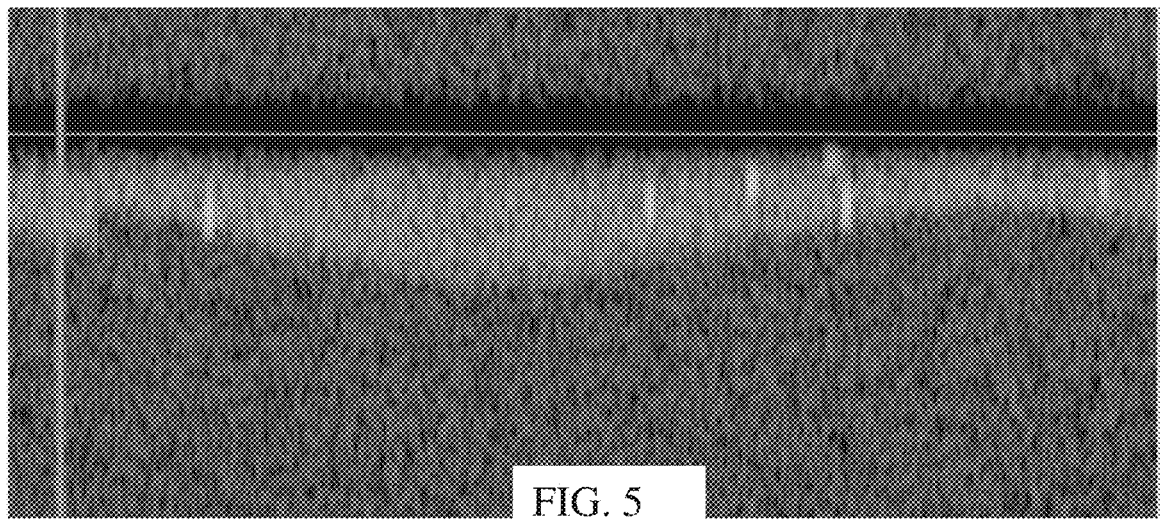
FIG. 5 shows an example of a spectral strip by estimating a single spectrum for each time for a Doppler gate.
Figure 6:
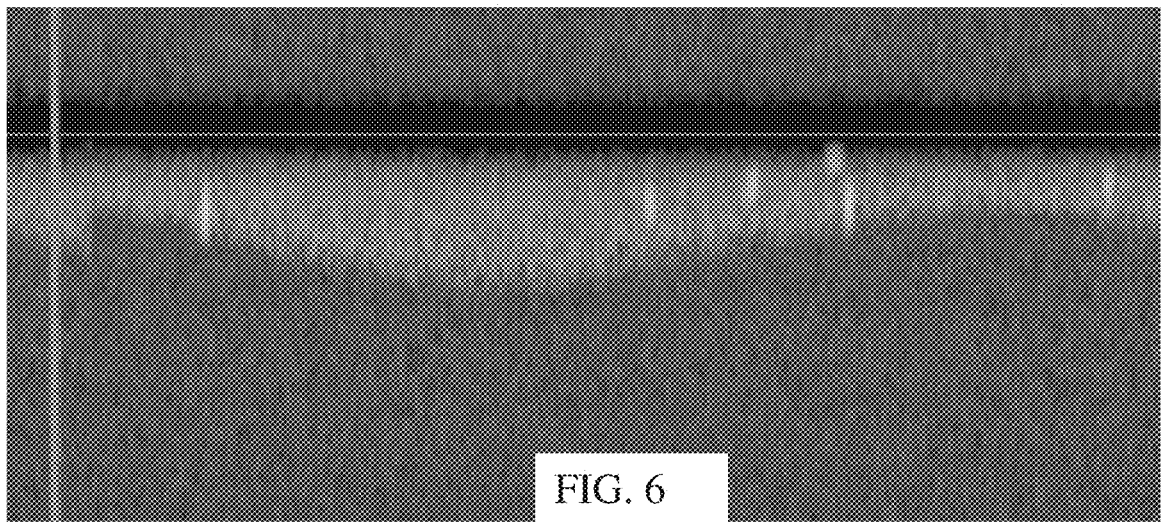
FIG. 6 shows an example of a spectral strip by combining spectra from different sub-gates of the Doppler gate of FIG. 5.

Acts 30, 34, and 36 are repeated for different times or periods. To create a spectral strip, a combined spectrum for each of different times is determined. FIGS. 5 and 6 show spectral strips of spectra for a same gate over time. The spectrum for a given time in a spectral strip is mapped with velocity on the horizontal axis and energy modulating the intensity. Other mapping may be used.

By repeating the acts, the combined spectra for the different times are acquired. As further samples are acquired, the further samples are added to the groups and old samples removed. A sequence of spectra for each group represents the Doppler gate at different times. Other spectra may be estimated for other periods or different times corresponding to different periods or ensembles of acquisition. The periods may overlap, such as when using a moving window with a step size less than the ensemble period, or may be unique. The acquisition of samples and estimating for a different period are repeated to provide spectra over time. For a spectral strip, the process and corresponding repetition is on-going or occurs multiple times.

Each spectrum of the spectral strip is formed from combining multiple spectra responsive to different spatial content. The groupings are used to estimate more than one spectrum for each time, allowing combination for the spectrum used in the spectral strip.

In act 38 of FIG. 1, the processor or Doppler estimator generates an image on a display. The image is a function of the spectra, such as shown in FIG. 6. The combined spectrum or series of combined spectra may be used to generate the spectral strip. The spectral strip is displayed for the Doppler gate. Filtering may be applied to smooth the spectra along the time and/or frequency dimensions or over energy. The spectral strip shows the frequency modulated by energy as a function of time. Any now known or later developed spectral strip mapping may be used, such as gray scale mapping with the intensity representing energy. The energies modulate the pixels. The gray scale or color is mapped from the energy values. The displayed image may be a function of a single combined spectrum or of multiple combined spectra.

In one embodiment, the spectral strip is displayed with a spatial image, such as a one-dimensional M-mode, two-dimensional B-mode, two-dimensional F-mode (flow mode), or combination thereof image. The location of the gate may be indicated graphically in the image, such as represented by a circle in the region of interest of the field of view. For example, text, color, symbol, or other indicator shows the location for the range gate corresponding to the spectral strip. Alternatively, the spectral strip is displayed without imaging from another mode.

The spectral strip of the image includes the combined spectra estimated with the velocity scale. The velocity scale defines a vertical range on the spectral strip. As additional samples are acquired, the resulting spectra for different times are added to the spectral strip, such as adding the spectra to a right side of the strip, shifting the remaining spectra one temporal step to the left, and removing the leftmost spectral strip. Each added spectrum is from a combination of information for spectra from the different groups. Other update or scrolling of the spectral strip may be used.

By combining the information from multiple spectra for each time, the amount of speckle or variance in the spectral strip may be reduced. Given at least partial independent noise or signal due to different spatial content, the noise, including speckle, may cancel or be reduced in variation. FIG. 5 shows a spectral strip for a range gate. The spectral strip is generated without separating the samples. The samples from various locations in the gate are accumulated and used to estimate one spectrum per period. FIG. 6 shows the spectral strip generated from the same samples as FIG. 5, but with the locations sub-divided into four sub-gates overlapped at 30%. In the examples of FIGS. 5 and 6, 35 sample locations are within the range gate and each sub-gate has 11 samples and starts from locations (by depth) 0, 8, 16, and 24, resulting in overlapped sub-gates by 3 samples. The spectral variance reduction in both noise and signal in FIG. 6 as compared to FIG. 5 may be easily appreciated. There are fewer and/or smaller blobs or speckle in FIG. 6. By combining the spectra for each time from the four groups, the amount of speckle or variation in the spectral strip is reduced.

In the embodiments above, pulsed wave spectral Doppler processing is used. In other embodiments, continuous wave spectral Doppler may be used. For continuous wave, the pulse repetition frequency does not apply as the transmission is continuous. Accordingly, the sub-gate or multiple line approaches may not apply. Instead, multiple-receive apertures are used to produce multiple spectra in the CW mode. These spectra may be combined.

FIG. 7 shows a system 10 for spectral pulsed wave Doppler imaging. The system 10 acquires responses at one or more locations, sampling responses from each location for estimating energy as a function of velocity or frequency. Groups of samples from a gate are acquired. Spectra are estimated from the samples of each group, providing spectra with different noise and/or signal variance. By combining the spectra representing the gate at the same time, a spectrum is provided with reduced signal and/or noise variation, resulting in an image that may be easier to use for diagnosis.

The system 10 is a medical diagnostic ultrasound imaging system. Other imaging systems may be used, such as a workstation loading samples from memory or other source.

The system 10 includes a transmit beamformer 12, a transducer 14, a receive beamformer 16, a Doppler processor 18, a display 20, a processor 21, and a memory 22. Additional, different or fewer components may be provided, such as the system 10 without the front-end beamformers 12, 16 and transducer 14 or the system 10 with a scan converter. The Doppler processor 18 and processor 21 may be combined into one device acting as both processors 18, 21, or additional processors for sequential or parallel processing may be used. A user input may be provided for placing the gate and/or sizing the gate.

The system 10 implements the method of FIG. 1. The beamformers 12, 16 and transducer 14 are used to acquire the samples with different spatial content. The Doppler processor 18 estimates the spectra for the gate from the samples with different spatial content for each time or period. The Doppler processor 18 and/or processor 21 combine the spectra and cause display of the combined spectrum on a display. Other methods may be implemented. The Doppler processing may be performed either before or after CINE.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit beamformer 12 is shown separate from the receive beamformer 16. Alternatively, the transmit and receive beamformers 12, 16 may be provided with some components in common. Operating together or alone, the transmit and receive beamformers 12, 16 form beams of acoustic energy for sampling a range gate and/or scanning a one, two, or three-dimensional region.

The transmit beamformer 12 is a processor, delay, filter, waveform generator, memory, phase rotator, digital-to-analog converter, amplifier, combinations thereof, or any other now known or later developed transmit beamformer components. In one embodiment, the transmit beamformer 12 digitally generates transmit waveform envelope samples. Using filtering, delays, phase rotation, digital-to-analog conversion and amplification, the desired transmit waveform is generated. In other embodiments, the transmit beamformer 12 includes switching pulsers or waveform memories storing the waveforms to be transmitted. Other transmit beamformers 12 may be used.

The transmit beamformer 12 is configured as a plurality of channels for generating electrical signals of a transmit waveform for each element of a transmit aperture on the transducer 14. The waveforms are unipolar, bipolar, stepped, sinusoidal, or other waveforms of a desired center frequency or frequency band with one, multiple, or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles, coding, or combinations thereof.

The transmit beamformer 12 is configured to transmit a sequence of transmit beams of ultrasound energy. A transmit beam originates from the transducer 14 at a location in the transmit aperture. The transmit beam is formed along a scan line at any desired angle. The acoustic energy is focused at a point along the scan line, but multiple points, line focus, no focus, or other spread may be used. The acoustic energy is directed at the Doppler gate, but may be focused elsewhere (e.g., the Doppler gate is along the scan line but not at the focus). The beam of acoustic energy is transmitted to the Doppler gate or to other locations.

For each gate, an ongoing sequence of transmit beams are generated at a PRF. The PRF determines the interval between temporally adjacent transmissions or transmit beams. The PRF may be low enough to have a period of no transmission not needed for travel time, interleaving with other imaging modes, and reverberation reduction. In one embodiment, the PRF is established based on the velocity scale, the travel time, interleaving, and reverberation reduction. In other embodiments, the PRF is set based on the velocity scale and the Nyquist criterion.

The receive beamformer 16 is a preamplifier, filter, phase rotator, delay, summer, base band filter, processor, buffers, memory, combinations thereof, or other now known or later developed receive beamformer component. Analog or digital receive beamformers capable of receiving one or more beams in response to a transmit event may be used.

The receive beamformer 16 is configured into a plurality of channels for receiving electrical signals representing echoes or acoustic energy impinging on the elements of the transducer 14. A channel from each of the elements of the receive aperture within the transducer 14 includes to an amplifier for applying apodization amplification. A controller selects the elements and corresponding channels to include in a given receive aperture. Some elements may be included in more than one receive aperture at a time. An analog-to-digital converter may digitize the amplified echo signal. The radio frequency receive data is demodulated to a base band frequency. Any receive delays, such as dynamic receive delays, and/or phase rotations are then applied by the amplifier and/or delay. A digital or analog summer combines data from different channels of the receive aperture to form a receive beam. The summer is a single summer or cascaded summers. The summer sums the relatively delayed and apodized channel information together to form a receive beam. Beamformed samples of echoes from the one or more locations are obtained, such as sampling at multiple locations along a receive scan line in a receive beam.

In one embodiment, the beamform summer is operable to sum in-phase and quadrature channel data in a complex manner such that phase information is maintained for the formed beam. Alternatively, the beamform summer sums data amplitudes or intensities without maintaining the phase information. Other receive beamformation may be provided, such as with demodulation to an intermediate frequency band and/or analog-to-digital conversion at a different part of the channel.

Beamforming parameters including a receive aperture (e.g., the number of elements and which elements used for given receive processing), the apodization profile, a delay profile, a phase profile, imaging frequency, inverse coding, or combinations thereof are applied to the receive signals for receive beamforming. For example, relative delays and amplitudes or apodization focus the acoustic energy along one or more scan lines. A control processor controls the various beamforming parameters for receive beamformation.

One or more receive beams are generated in response to each transmit beam. Acoustic echoes are received by the transducer 14 in response to the transmitted acoustic energy. The echoes are converted into electrical signals by the transducer 14, and the receive beamformer 16 forms the receive beams from the electrical signals to generate samples representing the location or locations within the range gate. The same receive echoes may be used to form receive beams along different scan lines and/or with different receive apertures.

Given the ongoing transmit beams at the PRF for each location, samples are generated in an ongoing manner as well. Responses over time are acquired for each of the locations and/or receive apertures. The responses for the different locations and/or receive apertures are responsive to the same transmit sequence, so create ensembles or accumulations of samples used to estimate spectra representing the same period.

The Doppler processor 18 is a spectral Doppler estimator. Other imaging detectors may be included, such as a B-mode detector. In one embodiment, the Doppler processor 18 is a digital signal processor or other device for applying a transform to the receive beam sample data. A sequence of transmit and receive events is performed over a period. A buffer (e.g., corner turning memory) or the memory 22 stores the receive beamformed data from each transmit and receive event. A wall filter, such as a programmable filter for distinguishing between tissue and fluid motion, may filter the samples prior to application of the transform. Any number of transmit and receive events may be used for determining a spectrum, such as three or more. The Doppler processor 18 estimates the spectra for the gate. By applying a discrete or fast Fourier transform or other transform to the ultrasound samples for the same gate, the spectra representing the responses from the gate are determined. Histograms or data representing the energy level at different frequencies for the period to acquire the samples are obtained. Velocity may be determined from the frequency or frequency is used without conversion to velocity.

By repeating the process, the Doppler processor 18 may obtain different spectra for a given gate at different times. Overlapping data may be used, such as calculating each spectrum with a moving window of selected ultrasound samples. Alternatively, each ultrasound sample is used for a single period and corresponding spectrum.

The Doppler processor 18 applies the transform for a range of frequencies. The range of frequencies or velocity scale limits the positive and negative velocities resulting from the estimation. Any of various velocity scales may be used, up to and including a velocity scale equal to the transmission PRF. The spectra are estimated using a given velocity scale. Similarly, the baseline or center of the velocity scale may be set.

The Doppler processor 18 may reduce noise and/or signal variance by combining spectra estimated from samples with different spatial content. The Doppler processor 18 is configured to generate multiple pulsed wave spectra from the sampling of the gate. Each pulsed wave spectrum for a given time or period is responsive to different spatial aspects of the gate. For example, each spectrum is generated from samples accumulated over time or during the ensemble sequence for different sets or groupings of locations sampled in the gate. As another example, each spectrum is generated from samples accumulated over time or during the ensemble sequence using different receive apertures. One of the multiple pulsed wave spectra is generated from the samples of one receive aperture, and another of the multiple pulsed wave spectra is generated from the samples of another of the receive apertures. The two or more receive apertures are overlapping or non-overlapping.

The processor 21 may be part of the Doppler processor 18 or a separate processor. The processor 21 is a general processor, control processor, digital signal processor, application specific integrated circuit, field programmable gate array, graphics processing unit, analog circuit, digital circuit, combinations thereof or other now known or later developed device for processing.

The processor 21 is configured to combine the pulsed wave spectra. The spectra estimated by the Doppler processor 18 for different spatial content are combined to reduce variance. The spectra are averaged or summed for combination. In alternative embodiments, the Doppler processor 18 performs the combination.

The processor 21, Doppler processor 18, or both processors 18, 21 are used for sample, location, or receive aperture selection, estimation and/or to control the imaging and/or system 10. The processor 21 is configured to perform and/or cause performance of various acts, such as the acts discussed above for FIG. 1. The processor 21 is configured, as part of or in communication with the Doppler processor 18. The processor 21 sets the PRF for the beamformers 12, 16 given a location of a Doppler gate relative to the transducer 14. The processor 21 generates or causes the Doppler processor 18 to generate the spectral strip. As the acquisition and estimation continue, spectra are added to the strip and old spectra are removed in a first-in, first-out scroll.

The processor 21 operates automatically. The user activates the spectral Doppler mode, indicates a velocity scale, indicates a baseline, may position the gate, and/or may size the gate. The speckle reduction is performed without further user input and/or without user input of values for one or more of the Doppler imaging parameters. In alternative embodiments, the user inputs the setting of the parameter, such as inputting a number of sub-gates. The processor 21 causes estimation of the spectra over time.

Additional processes, such as filtering, interpolation, and/or scan conversion, may be provided by the Doppler processor 18, the processor 21, or another device. The spectra are prepared and formatted for display. For example, the Doppler processor 18 generates display values as a function of the spectra estimated for the gate. Display values include intensity or other values to be converted for display (e.g., red, green, blue values) or analog values generated to operate the display 20. The display values may indicate intensity, hue, color, brightness, or other pixel characteristic. For example, the color is assigned as a function of one characteristic of a spectrum and the brightness is a function of another spectrum characteristic or other information. The display values are generated for a spectral strip display.

The display 18 is a CRT, monitor, LCD, plasma screen, projector or other now known or later developed display for displaying an image responsive to the combined spectrum or spectra. For a grey scale spectral Doppler image, a range of velocities with each velocity modulated as a function of energy is provided as a function of time. A given combined spectrum indicates the velocity and energy information for a given time. The intensity of a given pixel or pixel region represents energy where velocity is provided on the vertical scale and time provided on the horizontal scale. Other image configurations may be provided, including colorized spectral Doppler images. A color or flow mode image may be generated, such as showing mean velocity as a function of location in a region of interest in a grayscale B-mode.

The beamformers 12, 16, Doppler processor 18, and/or processor 21 are configured by hardware, software, firmware, or combinations thereof. Any configuration so that the device performs the act may be used.

The memory 22 stores ultrasound samples for the locations in the gate and/or for different receive apertures, stores estimated spectra, stores settings (e.g., values) for parameters, stores image data, or stores other information. The memory 22 may store information from any stage of processing or used for generating a display.

In one embodiment, the memory 22 is a non-transitory computer readable storage medium having stored therein data representing instructions executable by the programmed Doppler processor 18 and/or processor 21 for Doppler imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts, or tasks are independent of the particular type of instructions set, storage media, processor, or processing strategy and may be performed by software, hardware, integrated circuits, firmware, micro code or the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for spectral Doppler imaging, the method comprising:
    acquiring, with an ultrasound system, first and second sets of samples representing response from a single spatial region for a range gate positioned at one location with a gate size, the first and second sets of samples having first and second spatial content, respectively, the first spatial content different than the second spatial content;
    estimating, by a Doppler estimator, first and second spectra for the range gate from the samples of the first and second sets, respectively, the first and second spectra representing the response from the single spatial region at a same time;
    combining the two or more spectra into a combined spectrum representing the response from the single spatial region at the same time; and
    displaying a spectral Doppler strip with the combined spectrum representing the response from the single spatial region at the same time in the spectral Doppler strip.

2. The method of claim 1 wherein acquiring comprises transmitting with a pulse repetition frequency and acquiring samples for each of the sets in response to each repetition.

3. The method of claim 1 wherein acquiring comprises acquiring the first set of samples from a first sub-gate covering just a first part of the range gate and acquiring the second set of samples from a second sub-gate covering just a second part of the range gate, the first and second sub-gates defining the first and second spatial content.

4. The method of claim 3 wherein acquiring comprises acquiring with the first and second sub-gates overlapping but covering different ranges of depths within the range gate.

5. The method of claim 3 wherein acquiring comprises acquiring with the first and second sub-gates each comprising a set of contiguous beamform sample locations.

6. The method of claim 3 wherein acquiring comprises acquiring with the first and second sub-gates each comprising a set of dis-contiguous beamform sample locations.

7. The method of claim 1 wherein acquiring comprises forming the samples of the first and second sets with the first and second spatial content being responsive to transmits with reception using different receive apertures of a transducer array.

8. The method of claim 7 wherein forming comprises forming with the different receive apertures being overlapping on the transducer array.

9. The method of claim 1 wherein estimating comprises applying a Fourier transform to the samples of the first and second sets, the first and second spectra each comprising energy as a function of frequency over a range of the range gate.

10. The method of claim 1 wherein combining comprises summing the two or more spectra.

11. The method of claim 1 further comprising repeating the acquiring, estimating, and combining for different times, the different times for the repeating being other than the same time, and wherein displaying comprises displaying the spectral Doppler strip with each of the combined spectra representing the different times.

* * * * *